United States Patent [19]

Ernesto et al.

[11] Patent Number: 4,991,629
[45] Date of Patent: Feb. 12, 1991

[54] GAS-TIGHT CLOSURE DEVICE FOR THE CONNECTING ENDS OF TUBES FOR BIOMEDICAL FLUID-TRANSPORTING APPARATUS, PARTICULARLY HAEMODIALYSIS LINES, WHICH ARE STERILIZED BY MEANS OF STERILIZING GAS

[75] Inventors: Guala Ernesto; Beolchi Mario, both of Turin, Italy

[73] Assignee: Industrie Borla S.p.A., Turin, Italy

[21] Appl. No.: 248,016

[22] Filed: Sep. 23, 1988

[30] Foreign Application Priority Data

Sep. 25, 1987 [IT] Italy .................. 53672/87[U]
Nov. 4, 1987 [IT] Italy .................. 53790/87[U]

[51] Int. Cl.⁵ .................. F16L 55/10; B65D 59/06
[52] U.S. Cl. .................. 138/89; 138/96 R; 138/96 T; 604/256; 604/283
[58] Field of Search .................. 138/89, 96 T, 96 R; 128/766, 767, 768; 604/215, 256, 283, 404

[56] References Cited

U.S. PATENT DOCUMENTS

| | | | |
|---|---|---|---|
| 2,121,436 | 6/1938 | Lytle | 138/96 T |
| 2,930,118 | 3/1960 | Higgins | 138/96 T |
| 2,989,087 | 6/1961 | Higgins | 138/96 T |
| 3,876,234 | 4/1975 | Harms | 604/283 |
| 3,987,930 | 10/1976 | Luson | 138/89 |
| 4,335,756 | 6/1982 | Shapp et al. | 138/89 |
| 4,417,890 | 11/1983 | Dennehey et al. | 604/283 |
| 4,439,188 | 3/1984 | Dennehey et al. | 604/283 |
| 4,452,473 | 6/1984 | Ruschke | 604/283 |
| 4,629,455 | 12/1986 | Kanno | 604/283 |
| 4,809,752 | 3/1989 | Strödter | 138/96 T |
| 4,857,062 | 8/1989 | Russell | 604/256 |

*Primary Examiner*—James E. Bryant, III
*Attorney, Agent, or Firm*—Sughrue, Mion, Zinn, Macpeak & Seas

[57] ABSTRACT

A gas-tight closure device for the connecting ends of tubes for biomedical fluid-transporting apparatus, particularly haemodialysis lines, which are sterilized by means of sterilizing gas, includes a tubular connector defining an internal Luer cone and a cap which is fitted to the connector. The hermetic closure of the connector by the cap is effected by means of complementary conical surfaces for the mutual force-coupling of the outer lateral wall of the connector and the inner wall of the cap.

6 Claims, 3 Drawing Sheets

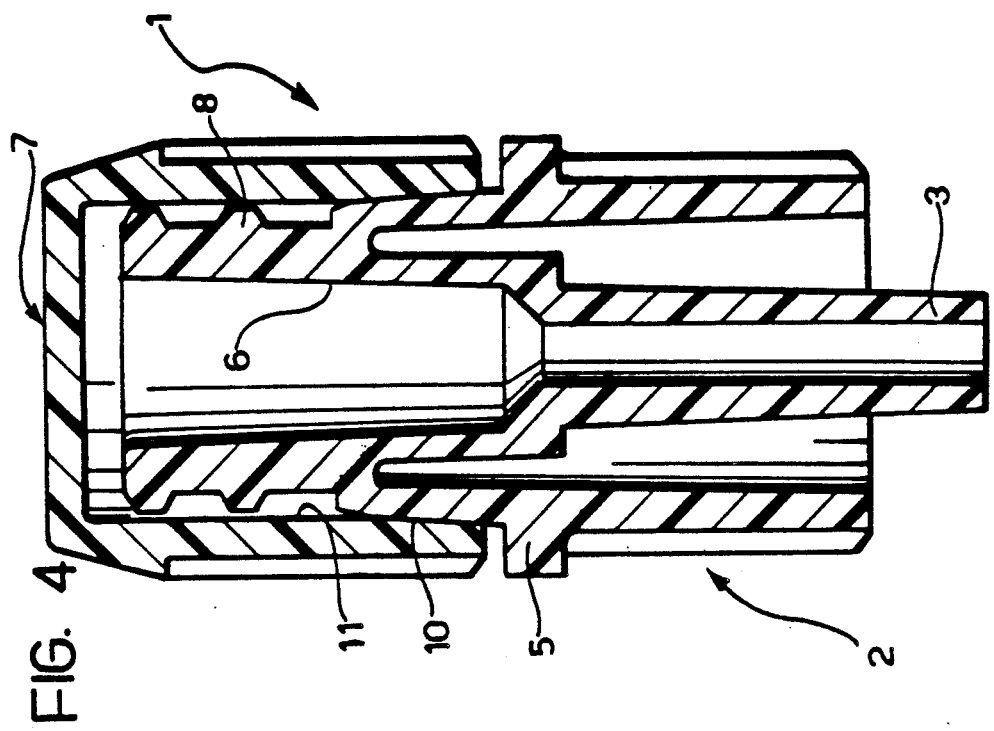
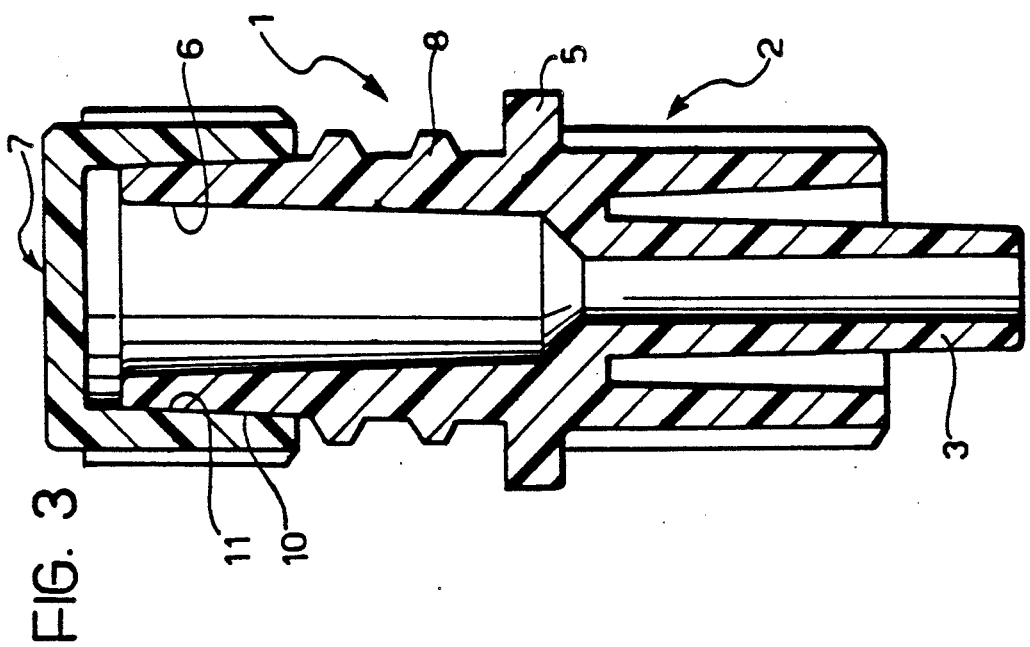

GAS-TIGHT CLOSURE DEVICE FOR THE CONNECTING ENDS OF TUBES FOR BIOMEDICAL FLUID-TRANSPORTING APPARATUS, PARTICULARLY HAEMODIALYSIS LINES, WHICH ARE STERILIZED BY MEANS OF STERILIZING GAS

BACKGROUND OF THE INVENTION

The present invention relates in general to biomedical fluid-transporting apparatus, particularly but not exclusively haemodialysis lines, including tubes which are sterilised by means of sterilising gas, normally ethylene oxide.

In order to maintain the working pressure within the line, the connecting ends of the tubes are provided with gas-tight closure devices.

The invention is particularly concerned with these gas-tight closure devices, which normally comprise a tubular connector having an internal Luer cone and provided with external screw-engagement projections, a cap which is fitted to the tubular connector, and hermetic sealing means between the cap and the tubular connector.

According to the prior art, the hermetic sealing means comprise (as will be described in greater detail below with reference to FIG. 6) an internal axial appendage of the cap, which has an outer conical surface complementary to that of the Luer cone of the connector and is adapted to be a force fit within the latter in the fitted condition of the cap.

Whilst it ensures the necessary gas-tight closure of the connecting end of the tube of the apparatus, this solution has the disadvantage that it prevents the gas introduced into the tube from sterilising that portion of the surface of the Luer cone against which the appendage of the body bears.

This results in incomplete sterilisation of the connector, with the risks which may ensue.

SUMMARY OF THE INVENTION

The object of the present invention is to avoid the above problem and to produce a gas-tight closure device of the type defined at the beginning, by means of which it is possible to achieve and maintain complete sterilisation of the tube to which it is applied.

According to the invention, this object is achieved by virtue of the fact that the hermetic sealing means between the cap and the tubular connector are arranged outside the Luer cone of the connector and include complementary conical surfaces for the mutual force-coupling of the outer lateral wall of the connector and the inner wall of the cap.

By virtue of this solution, the entire internal surface of the connector is effectively sterilised when the sterilising gas is introduced into the tube, whilst the closure effected by the cap remains hermetic.

The mutual coupling parts are normally constituted by complementary conical surfaces of the connector and the cap.

The conical surface of the connector may be situated upstream or downstream of the screw projections, with respect to the direction of fitting of the cap.

In both cases, the cap may be internally threaded so that it can be screwed onto the screw projections of the connector, or may lack internal threading.

According to a variant of the invention, the hermetic sealing means also include an inner annular projection of the cap which is adapted to be placed in frontal sealing contact against the end of the connector, around the mouth of the Luer cone.

BRIEF DESCRIPTION OF THE DRAWINGS

The invention will now be described in detail with reference to the appended drawings, in which:

FIGS. 2, 3, 4 and 5 show four possible variants of the device of FIG. 1.

DETAILED DESCRIPTION OF THE INVENTION

Figure 6:
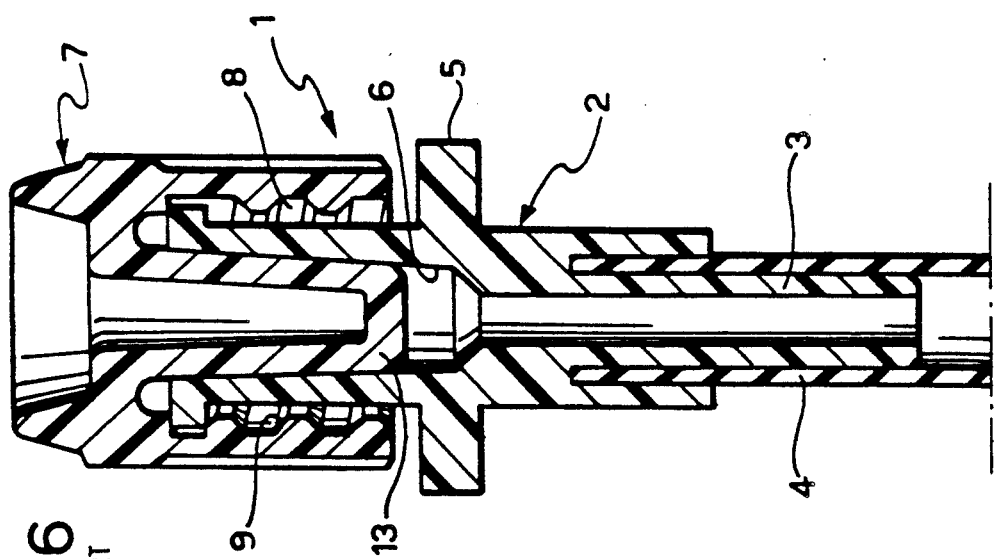
FIG. 6 is a view similar to FIG. 1 of a gas-tight closure device according to the prior art.

With reference initially to FIG. 6, a gas-tight closure device according to the prior art for the connecting ends of tubes for biomedical fluid-transporting apparatus, for example, haemodialysis lines, which are sterilised by means of ethylene oxide or similar sterilisation gases, is generally indicated 1.

The connecting end is constituted by a tubular connector 2 of moulded plastics material having, at one, a tubular appendage 3 which is slightly tapered and is force-fitted into the end of a flexible tube 4. The opposite end of the connector 2, which is normally separated from the tubular appendage 3 by means of a radial flange 5, forms an internal Luer cone 6 of conventional type, constituting a connecting end of the connector 2.

In order to ensure the hermetic sealing of the connector 2, so as to prevent the escape of the sterilisation gas until the time when the apparatus is used, a closure cap 7 is provided and is fitted to the outside of the connector 2 in the region of the Luer cone 6.

The known cap 7 has internal threading 9 which is screwed onto corresponding external screw-engagement projections 8 of the connector 2, and an inner axial appendage 13 whose conical shape is complementary to that of the Luer cone 6. When the cap 7 is screwed onto the connector 2, the inner appendage 10 of the cap 7 is force-fitted into the Luer cone 6, so as to effect the gas-tight closure thereof and thus enable the sterilisation gas to be introduced into the tube 4 and retained therein. However, it is obvious that the region of the outer surface of the Luer cone 6 against which the outer surface of the appendage 10 of the cap 7 bears cannot be reached by the sterilisation gas and cannot consequently be sterilised, with the risks which ensue.

This problem is avoided by the gas-tight closure device according to the invention illustrated in FIGS. 1 to 5, in which parts identical or similar to those described with reference to FIG. 6 are indicated by the same reference numerals.

Unlike the prior art, according to the invention, the hermetic sealing of the connector 2 by the cap 7 is effected outside the Luer cone 6, and in the case of FIGS. 1 to 4 solely by means of parts for the mutual force-coupling of the outer wall of the connector 2 and the inner wall of the cap 7.

Figure 1:
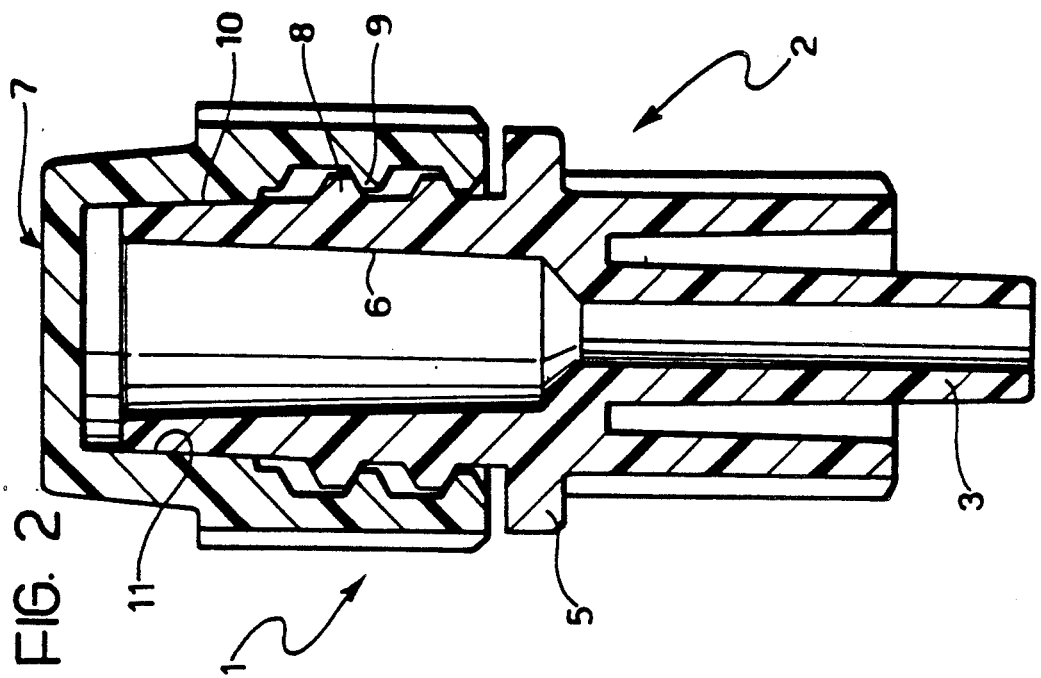
FIG. 1 is a schematic axial sectional view of a gas-tight closure device according to a first embodiment of the invention.

In the case of FIG. 1, these mutual force-coupling parts are constituted by an outer conical surface 10 of the connector 2, interposed between the flange 5 and the screw projections 8, and a corresponding inner conical surface 11 extending from the end edge of the cap 7.

With this solution, the entire surface of the Luer cone 6 may be sterilised effectively by the sterilisation gas introduced into the tube 4 and the escape of the sterilisation gas is effectively prevented by the lateral seal constituted by the complementary surfaces 10 and 11.

Figure 2:
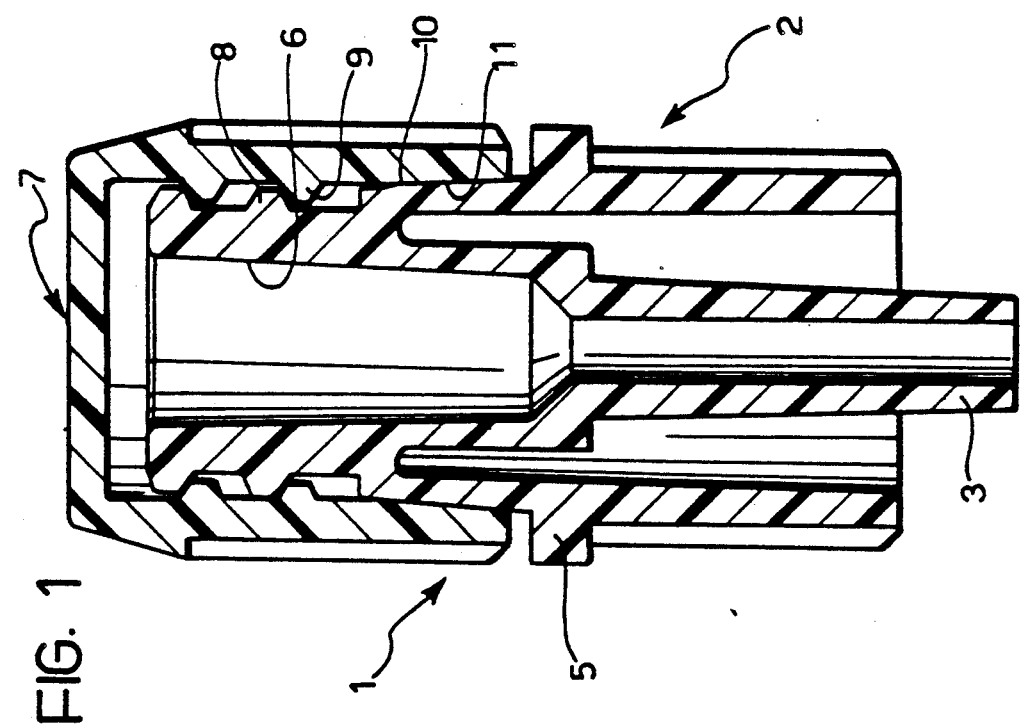

FIGS. 2 to 4 show three possible variants of the hermetic sealing system between the connector 2 and the cap 7, which fall within the scope of the concept consisting of the provision of parts solely for the lateral sealing of the two elements. In these drawings, elements identical or similar to those already described with reference to FIG. 1 are indicated by the same reference numerals.

The version of FIG. 2 differs from that described above only in that the outer conical surface 10 of the connector 2 is formed near the mouth of the Luer cone 6, that is, upstream of the screw-engagement projections 8 with respect to the direction of fitting of the cap 7. The conical surface of the latter is formed correspondingly near the end of the cap 7.

This same configuration is used in the embodiment shown in FIG. 3, which differs from that of FIG. 2 only in that the cap 7 has no internal threading. In this case, the cap 7 is retained on the connector 2 simply by the force-coupling between the conical surfaces 10 and 11.

In the case of FIG. 4, the coupling surfaces 10 and 11 are positioned as in the case of FIG. 1: however, in this variant also, the cap lacks internal threading and is retained as in the case of FIG. 1: however, in this variant also, the cap lacks internal threading and is retained by the force-coupling between the surfaces 10 and 11, as in the case of FIG. 3.

Figure 5:
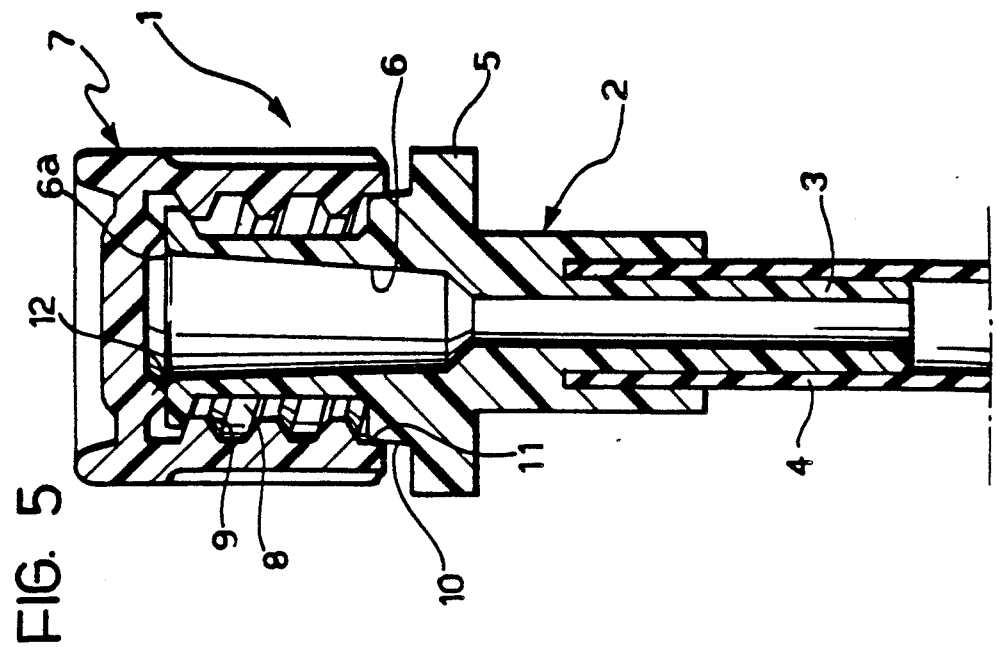

In the case of FIG. 5, the hermetic sealing of the connector 2 by the cap 7 is effected, again externally of the Luer cone 6, both frontally and laterally against the outer surface of the connector 2 in the region of the cone 6. The frontal seal is effected by means of an inner annular projection 12 of the cap 7 which, when the latter is screwed onto the connector 2, bears against the end of the connector 2, around the mouth 6a of the cone 6.

The lateral sealing is effected by means of an external enlargement 10 of the connector 2, which is spaced axially from the screw-engagement projections 9 and against the slightly conical outer surface of which the complementary conical surface of the end part 11 of the inner wall of the cap 7 is force-fitted in the screwed-on condition.

What is claimed is:

1. A gas-tight closure device for the connecting ends of tubes for biomedical fluid-transporting apparatus, particularly but not exclusively haemodialysis lines, which are sterilised by means of sterilising gas, comprising a tubular connector having an end surface, an internal Luer cone and an outer lateral wall provided with external screw-engagement projections, a cap having an inner wall which is fitted to the tubular connector, and hermetic sealing means between the cap an the tubular connector, wherein the hermetic sealing means are only situated outside the Luer cone of the connector and include complementary conical surfaces defined by the outer lateral wall of the connector and the inner wall of the cap for mutual sealing engagement.

2. A device according to claim 1, wherein the conical surface of the connector is located between said end surface and said screw projections.

3. A device according to claim 1, wherein the screw projections on said connector are located between said end surface and said conical surface.

4. A device according to claim 1, wherein the cap is provided with internal threading for screwing onto the screw projections of the connector.

5. A device according to claim 1, wherein the cap is not internally threaded.

6. A device according to claim 1, wherein the hermetic sealing means also include an inner annular projection on the cap which is adapted to be placed in frontal sealing contact against the end surface of the connector.

* * * * *